(12) United States Patent
Sailor et al.

(10) Patent No.: US 8,765,484 B2
(45) Date of Patent: Jul. 1, 2014

(54) OPTICALLY ENCODED PARTICLES

(75) Inventors: Michael J. Sailor, San Diego, CA (US);
Thomas Schmedake, Charlotte, NC (US); Frederique Cunin, Cardiff, CA (US); Jamie Link, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1075 days.

(21) Appl. No.: 10/503,217

(22) PCT Filed: Jan. 31, 2003

(86) PCT No.: PCT/US03/03040
§ 371 (c)(1),
(2), (4) Date: Aug. 2, 2004

(87) PCT Pub. No.: WO03/067231
PCT Pub. Date: Aug. 14, 2003

(65) Prior Publication Data
US 2005/0042764 A1    Feb. 24, 2005

Related U.S. Application Data

(60) Provisional application No. 60/355,234, filed on Feb. 7, 2002.

(51) Int. Cl.
*G01N 33/50* (2006.01)
*G01N 33/552* (2006.01)
*G01N 21/55* (2014.01)
*G01N 37/00* (2006.01)
*C12Q 1/68* (2006.01)

(52) U.S. Cl.
USPC .... 436/171; 422/68.1; 422/82.05; 422/82.06; 422/82.07; 422/82.08; 435/6.11; 436/56; 436/86; 436/94; 436/95; 436/166; 436/172; 436/518; 436/524; 436/527

(58) Field of Classification Search
USPC ......... 436/166, 172, 56, 86, 94–95, 518, 524, 436/527; 435/6, 6.11; 205/118, 122; 422/68.1, 82.05–82.08
See application file for complete search history.

(56) References Cited

U.S. PATENT DOCUMENTS 1,822,098 A  *  9/1931  Huntress ................. 428/378
3,733,178 A  *  5/1973  Eriksen ................... 436/56
(Continued)

FOREIGN PATENT DOCUMENTS

| EP | 927749 | * | 7/1999 |
| WO | WO/83/00395 | | 2/1983 |
| WO | WO/03/067231 | | 8/2003 |
| WO | WO 2006/050221 | | 5/2006 |

OTHER PUBLICATIONS

Fauchet, P. M., Journal of Luminescence 1999, 80, 53-64.*
Squire, E. K., Journal of Luminescence 1999, 80, 125-128.*

(Continued)

*Primary Examiner* — Arlen Soderquist
(74) *Attorney, Agent, or Firm* — Greer, Burns & Crain Ltd.

(57) ABSTRACT

The invention concerns a particle having a code embedded in its physical structure by refractive index changes between different regions of the particle. In preferred embodiments, a thin film possesses porosity that varies in a manner to produce a code detectable in the reflectivity spectrum.

27 Claims, 11 Drawing Sheets

(56) References Cited

U.S. PATENT DOCUMENTS

| | | | | |
|---|---|---|---|---|
| 3,772,099 | A | * | 11/1973 | Ryan et al. ............... 149/18 |
| 3,858,977 | A | * | 1/1975 | Baird et al. ............... 356/71 |
| 3,861,886 | A | * | 1/1975 | Meloy ............................ 436/56 |
| 3,897,284 | A | * | 7/1975 | Livesay ........................ 149/21 |
| 4,053,433 | A | * | 10/1977 | Lee ............................ 252/408.1 |
| 4,131,064 | A | * | 12/1978 | Ryan et al. .................. 102/293 |
| 4,197,104 | A | * | 4/1980 | Krystyniak et al. ........... 65/21.3 |
| 4,329,393 | A | * | 5/1982 | LaPerre et al. ................ 428/325 |
| 4,387,112 | A | * | 6/1983 | Blach ................................ 427/7 |
| 4,390,452 | A | * | 6/1983 | Stevens ..................... 252/408.1 |
| 4,434,010 | A | * | 2/1984 | Ash ................................ 106/415 |
| 4,780,423 | A | * | 10/1988 | Bluestein et al. ............ 436/527 |
| 4,879,140 | A | * | 11/1989 | Gray et al. .................... 427/490 |
| RE33,581 | E | | 4/1991 | Nicoli et al. |
| 5,071,248 | A | | 12/1991 | Tiefenthaler et al. |
| 5,118,369 | A | * | 6/1992 | Shamir ........................... 156/64 |
| 5,135,812 | A | * | 8/1992 | Phillips et al. ................ 428/403 |
| 5,168,104 | A | * | 12/1992 | Li et al. .......................... 521/64 |
| 5,218,472 | A | | 6/1993 | Jozefowicz et al. |
| 5,301,204 | A | * | 4/1994 | Cho et al. ....................... 372/69 |
| 5,318,676 | A | | 6/1994 | Sailor et al. |
| 5,350,715 | A | * | 9/1994 | Lee ................................. 438/16 |
| 5,468,606 | A | | 11/1995 | Bogart et al. |
| 5,512,162 | A | | 4/1996 | Sachs et al. |
| 5,696,629 | A | * | 12/1997 | Berger et al. ................. 359/582 |
| 5,763,176 | A | | 6/1998 | Slater et al. |
| 5,928,726 | A | | 7/1999 | Butler et al. |
| 5,974,150 | A | * | 10/1999 | Kaish et al. .................... 713/179 |
| 6,010,751 | A | * | 1/2000 | Shaw et al. ................. 427/255.7 |
| 6,060,143 | A | | 5/2000 | Tompkin et al. |
| 6,060,240 | A | * | 5/2000 | Kamb et al. ..................... 506/4 |
| 6,096,496 | A | * | 8/2000 | Frankel ........................... 506/31 |
| 6,130,748 | A | * | 10/2000 | Kruger et al. ................. 356/450 |
| 6,206,065 | B1 | * | 3/2001 | Robbie et al. ................. 156/349 |
| 6,248,539 | B1 | | 6/2001 | Ghadiri et al. |
| 6,255,709 | B1 | * | 7/2001 | Marso et al. ................... 257/462 |
| 6,355,431 | B1 | | 3/2002 | Chee et al. |
| 6,393,868 | B1 | * | 5/2002 | Krauss et al. ..................... 65/23 |
| 6,396,995 | B1 | | 5/2002 | Stuelpnagel et al. |
| 6,429,027 | B1 | | 8/2002 | Chee et al. |
| 6,473,165 | B1 | * | 10/2002 | Coombs et al. ................. 356/71 |
| 6,544,732 | B1 | | 4/2003 | Chee et al. |
| 6,572,784 | B1 | * | 6/2003 | Coombs et al. ........... 252/301.16 |
| 6,620,584 | B1 | | 9/2003 | Chee et al. |
| 6,630,356 | B1 | * | 10/2003 | Armstrong et al. ........... 436/172 |
| 6,643,001 | B1 | * | 11/2003 | Faris ................................ 356/37 |
| 6,663,832 | B2 | | 12/2003 | Lebl et al. |
| 6,678,619 | B2 | | 1/2004 | Lobanov et al. |
| 6,690,027 | B1 | * | 2/2004 | Bensahel et al. ................ 257/14 |
| 6,761,959 | B1 | * | 7/2004 | Bonkowski et al. ........... 428/156 |
| 6,770,441 | B2 | | 8/2004 | Dickinson et al. |
| 6,778,272 | B2 | * | 8/2004 | Nakano et al. ................. 356/336 |
| 6,812,005 | B2 | | 11/2004 | Fan et al. |
| 6,846,460 | B1 | | 1/2005 | Lebl |
| 6,858,394 | B1 | | 2/2005 | Chee et al. |
| 6,919,009 | B2 | * | 7/2005 | Stonas et al. .................... 205/74 |
| 6,924,033 | B2 | | 8/2005 | Pryor et al. |
| 7,042,570 | B2 | | 5/2006 | Sailor et al. |
| 7,162,035 | B1 | * | 1/2007 | Durst et al. ...................... 380/54 |
| 7,225,082 | B1 | * | 5/2007 | Natan et al. ..................... 702/27 |
| 7,226,733 | B2 | * | 6/2007 | Chan et al. ........................ 435/6 |
| 7,238,424 | B2 | * | 7/2007 | Raksha et al. ................. 428/403 |
| 7,241,629 | B2 | * | 7/2007 | Dejneka et al. ................ 436/525 |
| 7,433,811 | B2 | | 10/2008 | Gao et al. |
| 2002/0084329 | A1 | * | 7/2002 | Kaye et al. ................. 235/462.01 |
| 2002/0192680 | A1 | * | 12/2002 | Chan et al. ........................ 435/6 |
| 2003/0119059 | A1 | * | 6/2003 | Still et al. ....................... 435/7.1 |
| 2003/0124564 | A1 | * | 7/2003 | Trau et al. ......................... 435/6 |
| 2003/0146109 | A1 | | 8/2003 | Sailor et al. |
| 2003/0170280 | A1 | * | 9/2003 | Canham et al. ................ 424/401 |
| 2003/0203390 | A1 | * | 10/2003 | Kaye et al. ........................ 435/6 |
| 2004/0023253 | A1 | | 2/2004 | Kunwar et al. |
| 2004/0244889 | A1 | | 12/2004 | Sailor |
| 2005/0003098 | A1 | | 1/2005 | Kohler et al. |
| 2005/0003556 | A1 | * | 1/2005 | Nagasawa et al. ............ 436/518 |
| 2006/0051872 | A1 | | 3/2006 | Sailor |
| 2006/0063074 | A1 | | 3/2006 | Jenson et al. |
| 2006/0105043 | A1 | | 5/2006 | Sailor |
| 2006/0236436 | A1 | | 10/2006 | Li |
| 2006/0255008 | A1 | | 11/2006 | Sailor |
| 2007/0051815 | A1 | | 3/2007 | Sailor |
| 2007/0108465 | A1 | | 5/2007 | Pacholski |
| 2007/0148695 | A1 | | 6/2007 | Sailor |
| 2008/0145513 | A1 | | 6/2008 | Li |
| 2008/0212068 | A1 | | 9/2008 | Sailor |
| 2008/0296255 | A1 | | 12/2008 | Sailor |

OTHER PUBLICATIONS

Mattei, G. et al, Surface Science 1999, 427-428, 235-238.*
Setzu, S. et al, Materials Science and Engineering 2000, B69-70, 34-42.*
Zhou, Y. et al, Physica Staus Solidi A 2000, 182, 319-324.*
Letant, S. E. et al, Advanced Materials 2001, 13, 335-338.*
Lammel, G. et al, Sensors and Actuators A 2001, 92, 52-59.*
Pavesi, L. et al, Journal of Applied Physics 1994, 75, 1118-1126.*
Berger, M. G. et al, Journal of Physics D: Applied Physics 1994, 27, 1333-1336.*
Vincent, G., Applied Physics Letters 1994, 64, 2367-2369.*
Mazzoleni, C. et al, Applied Physics Letters 1995, 67, 2983-2985.*
Janshoff, A. et al, Journal of the American Chemical Society 1998, 120, 12108-12116.*
Credo, G. M. et al, Applied Physics Letters 1999, 74, 1978-1980.*
Snow, P. A. et al, Journal of Applied Physics 1999, 86, 1781-1784.*
Chan, S. et al, SPIE 2000, 3912, 23-34.*
Diener, J. et al, Applied Physics Letters 2001, 78, 3887-3889.*
Chan, S. et al, Journal of the American Chemical Society 2001, 123, 11797-11798.*
Berger, M. G. et al, Thin Solid Films 1995, 255, 313-316.*
Hilbrich, S. et al, Thin Solid Films 1997, 297, 250-253.*
Song, J. H. et al, Journal of the American Chemical Society 1997, 119, 7381-7385.*
Nashat, A. H. et al, Biotechnology and Bioengineering 1998, 60, 137-146.*
Marso, M. et al, Thin Solid Films 2001, 382, 218-221.*
Talapin, D. V. et al, Nano Letters 2001, 1, 207-211.*
Gottlich, H. et al, Ultramicroscopy 1995, 61, 145-153.*
Bley, R. A. et al, Chemistry of Materials 1996, 8, 1881-1888.*
Chan, S. et al, Applied Physics Letters 1999, 75, 274-276.*
Berger, M. G. et al, SPIE 1994, 2253, 865-871.*
Pavesi, L., Physica Status Solidi A 1998, 165, 91-96.*
Alieva, E. V. et al, Physica Status Solidi A 1999,175,115-120.*
Golovan, L. A. et al, Physica Status Solidi A 2000, 182, 437-442.*
Kruger, M. et al, Thin Solid Films 1997, 297, 241-244.*
Eric J. Lee et al., "Photoderivation of the Surface of Luminescent Porous Silicon with Formic Acid", *J. Am. Chem. Soc.*, vol. 117, 8295-96 (1995).
V.S.Y. Lin et al., "A Porous Silicon-Based Optical Interferometric Biosensor", *Science*, vol. 278, pp. 840-842 (Oct. 31, 1997).
Andreas Janshoff et al., "Macroporous p-Type Siicon Fabry-Perot Layers. Fabrication, Characterization, and Applicationsin Biosensing", *J. Am. Chem. Soc.*, vol. 120, pp. 12108-12116 (1998).
S. R. Nicewarner-Peña et al., "Submicrometer Metallic Barcodes", *Science*, vol. 294, pp. 137-141 (Oct. 5, 2001).
L. Pavesi et al., "Random Porous Silicon Multilayers: Application to Distributed Bragg Reflectors and Interferential Fabry-Pérot Filters", *Semicond. Sci. Technol.*, vol. 12, pp. 570-575 (1997).
D. Van Noort et al., "Monitoring Specific Interaction of Low Molecular Weight Biomolecules on Oxidized Porous Silicon Using Ellipsometry", *Biosensors & Bioelectronics*, vol. 13, No. 3-4, pp. 439-449 (1998).
M. Thonissen et al., Section 1.4, "Multilayer Structures of Porous Silicon", In *Properties of Porous Silicon*, (Eds: L. Canham). EMIS Datareviews, vol. 8, Short Run Press Ltd., London, pp. 30-37 (1997).
Honglae Sohn et al., "Detection of Fluorophosphonate Chemical Warefare Agents by Catalytic Hydrolysis with a Porous Silicon Interferometer", *J. Am. Chem. Soc.*, vol. 122, pp. 5399-5400 (2000).

(56) References Cited

OTHER PUBLICATIONS

M.J. Sailor, "Sensor Applications of Porous Silicon", Section 12.4, In *Properties of Porous Silicon*, (Eds: L. Canham). EMIS Datareviews, vol. 8, Short Run Press Ltd., London, pp. 364-370 (1997).

J.R. Quagliano et al., "Quantitative Chemical Identification of Four Gases in Remote Infrared (9-11 µm) Differential Absorption Lidar Experiments", *Applied Optics*, vol. 36, No. 9, pp. 1915-1927 (Mar. 20, 1997).

M.J. Sailor et al., "Low-Power Microsenors for Explosives and Nerve Warfare Agents Using Silicon Nanodots and Nanowires", In SPIE Meeting on Unattended Ground Sensor Technologies and Applications, (Ed: E.M. Carapezza, D.B. Law and K.T. Stalker). SPIE, 2000.

B. Warneke et al., "Smart Dust: Communicating with a Cubic-Millimeter Computer", *Computer*, pp. 44-51 (Jan. 2001).

V.G. Cheung et al., "Making and Reading Microarrays", *Nature Genetics Supplement*, vol. 21, pp. 15-19, (Jan. 1999).

L.T. Canham et al., "Derivatized Porous Silicon Mirrors: Implantable Optical Components with Slow Resorbability", *Physica*, vol. 182, No. 1, pp. 521-525 (2000).

A.P. Bowditch, "In-Vivo Assessment of Tissue Compatibility and Calcification of Bulk and Porous Silicon", *Materials Research Society Symp. Proc.*, vol. 536, pp. 149-154 (1999).

S. Chan et al., "Porous Silicon Microcavities for Biosensing Applications", *Phys. Stat. Sol.*, vol. 182, pp. 541-546 (2000).

"Abstracts of Oak Ridge Posters", *Clinical Chem.*, vol. 46, No. 9, pp. 1487-1522 (2000).

K.P.S. Dancil et al., "A Porous Silicon Optical Biosensor: Detection of Reversible Binding of IgG to a Protein A-Modified Surface," *J. Am. Chem. Soc.*, vol. 121, pp. 7925-7930 (1999).

J.H. Holtz et al., "Polymerized Colloidal Crystal Hydrogel Films as Intelligent Chemical Sensing Materials", *Nature*, vol. 389, pp. 829-832 (Oct. 23, 1997).

J. Gao et al., "Porous-Silicon Vapor Sensor Based on Laser Interferometry", *Applied Physics Letters*, vol. 77, No. 6, pp. 901-903 (Aug. 7, 2000).

J.M. Lauerhaas et al., "Chemical Modification of the Photoluminescence Quenching of Porous Silicon", *Science*, vol. 261, pp. 1567-1568 (Sep. 17, 1993).

J.L. Heinrich et al., "Luminescent Colloidal Silicon Suspensiosn from Pourous Silicon", *Science*, vol. 255, No. 5040, pp. 66-68 (Jan. 3, 1992).

M.D. Ray et al., "Ultraviolet Mini-Raman Lidar for Stand-Off, in situ, Identification of Chemical Surface Contaminants", *Review of Scientific Instruments*, vol. 71, No. 9, pp. 3485-3489 (Sep. 2000).

N.F. Starodub et al., "Use of the Silicon Crystals Photoluminescence to Control Immunocomplex Formation", *Sensors and Actuators*, pp. 44-47, (1996).

M.J. Sailor et al., "Detection of DNT, TNT, HF and Nerve Agents Using Photoluminescence and Interferometry from a Porous Silicon Chip", In *Unattended Ground Senor Technologies and Applications II*, Proceedings of SPIE, vol. 4040, pp. 95-104 (2000).

L. Pavesi et al., "Controlled Photon Emission in Porous Silicon Microcavities", *Appl. Phys. Lett.*, vol. 67, No. 22, pp. 3280-3282 (Nov. 27, 1995).

C. Mazzoleni et al., "Application to Optical Components of Dielectric Porous Silicon Multilayers", *Appl. Phys. Lett.*, vol. 67, No. 20, pp. 2983-2985 (Nov. 13, 1995).

V. Lehmann et al., "Optical Shortpass Filters Based on Macroporous Silicon", *Applied Physics Letters*, vol. 78, No. 5, pp. 589-591 (Jan. 29, 2001).

A.M. Tinsley-Bown et al., "Tuning the Pore Size and Surface Chemistry of Porous Silicon for Immunoassays", *Phys. Stat. Sol.*, vol. 182, pp. 547-553 (2000).

P.A. Snow et al., "Vapor Sensing using the Optical Properties of Porous Silicon Bragg Mirrors", *Journal of Applied Physics*, vol. 86, No. 4, pp. 1781-1784 (Aug. 15, 1999).

G. Vincent, "Optical Properties of Porous Silicon Superlattices", *Appl. Phys. Lett.*, vol. 64, No. 18, pp. 2367-2369 (May 2, 1994).

V. Wulmeyer et al., "Ground-Based Differential Absorption Lidar for Water-Vapor Profiling: Assessment of Accuracy, Resolution, and Meteorological Applications", *Applied Optics*, vol. 37, No. 18, pp. 3825-3844 (Jun. 20, 1998).

M. Bruchez, Jr. et al., "Semiconductor Nanocrystals as Fluorescent Biological Labels", *Science*, vol. 281, pp. 2013-2016 (Sep. 25, 1998).

C.B. Carlisle et al., "$CO_2$ Laser-Based Differential Absorption Lidar System for Range-Resolved and Long-Range Detection of Chemical Vapor Plumes", *Applied Optics*, vol. 34, No. 27, pp. 6187-6200 (Sep. 20, 1995).

S. Chan et al., "Identification of Gram Negative Bacteria Using Nanoscale Silicon Microcavities", *J. Am. Chem. Soc.*, vol. 123, No. 47, pp. 11797-11798 (2001).

C.L. Curtis et al., "Observation of Optical Cavity Modes in Photoluminescent Porous Silicon Films", *J. Electrochem. Soc.*, vol. 140, No. 12, pp. 3492-3494 (Dec. 1993).

S. Content et al., "Detection of Nitrobenzene, DNT, and TNT Vapors by Quenching of Porous Silicon Photoluminescence", *Chem. Eur. J.*, vol. 6, No. 12, pp. 2205-2213 (2000).

D. Gerion et al., "Synthesis and Properties and Biocompatible Water-Soluble Silica-Coated CdSe/ZnS Semiconductor Quantum Dots", *J. Phys. Chem. B*, vol. 105, pp. 8861-8871 (2001).

M.R. Henry, et al., "Real-Time Measurements of DNA Hybridization on Microparticles with Fluorescence Resonance Energy Transfer", *Analytical Biochemistry*, vol. 276, pp. 204-214 (1999).

P. Coronado et al., "New Technologies to Support NASA's Mission to Planet Earth Satellite Remote Sensing Product Validation: The Use of an Unmanned Autopilotd Vehicle (UAV) as a Platform to Conduct Remote Sensing", Part of the SPIE Conference on Robotic and Semi-Robotic Ground Vehicle Technology, Orlando, FL Apr. 1998, vol. 3366, pp. 38-49.

D.F. Shriver, "The Manipulation of Air-Sensitive Compounds", 2d Ed., John Wiley & Sons, Inc. New York, 1986, pp. 290-311.

F. Cunin et al., "Biomolecular Screening with Encoded Porous-Silicon Photonic Crystals", Nature Materials, vol. 1, pp. 39-41. (Sep. 2002).

M.G. Berger et al., "Dielectric Filter Made of Porous Silicon: Advanced Performance by Oxidation and New Layer Structures", Thin Solid Films, vol. 297, pp. 237-240 (1997).

H. . Fenniri et al., J. Am. Chem. Soc., vol. 123, pp. 8151-8152 (2001).

H. Fenniri et al., Angew. Chem. Int. Ed., vol. 39, pp. 4483-4485 (2000).

W.C.W. Chan et al., "Quantum Dot Bioconjugates for Ultrasensitive Nonisotopic Detection", Science, vol. 281, pp. 2016-2018 (1998).

J.A. Ferguson et al., "A Fiber Optic DNA Biosensor Microarray for the Analysis of Gene Expression", Nature Biotechnol, vol. 14, pp. 1681-1684 (1996).

M. Thonissen et al., Properties of Porous Silicon, vol. 18, pp. 12-22, (ed. L. Canham) (Short Run, London 1997).

A. Halimaoui, Properties of Porous Silicon, vol. 18, pp. 12-22, (ed. L. Canham) (Short Run, London 1997).

J. Vuckovic et al., "Optimization of Three-Dimensional Micropost Microcavities for Cavity Quantum Electrodynamics", Physical Review A., vol. 66, 2002, pp. 023808-1-023808-9.

Ruminski, Anne M., "Internally Referenced Remote Sensors for HF and $CL_2$ Using Reactive Porous Silicon Photonic Crystals", *Advanced Functional Materials*, 2011, 1511-1525, vol. 21.

Ruminski, Anne M., "Humidity-Compensating Sensor for Volatile Organic Compounds Using Stacked Porous Silicon Photonic Crystals", *Advanced Functional Materials*, 2008, 3418-3426, vol. 18.

Thonissen, M., et al., "Mulitlayer Structures of Porous Silicon", May 1997, 30-37.

Berger, Patricia, et al, "Preparation and Properties of an Aqueous Ferrofluid", *Journal of Chemical Education*, Jul. 1999, vol. 76: No. 7.

* cited by examiner

US 8,765,484 B2

OPTICALLY ENCODED PARTICLES

PRIORITY CLAIM

Applicants claim priority benefits under 35 U.S.C. §119 on the basis of Patent Application No. 60/355,234, filed Feb. 7, 2002.

STATEMENT OF GOVERNMENT INTEREST

This invention was made with Government assistance under contract number 20-5015 awarded by NIH and contract number N66001-98-C-8514 awarded by DARPA. The Government has certain rights in this invention.

FIELD OF THE INVENTION

A field of the invention is encoding. Additional exemplary fields of the invention include the life sciences, security, product marking, food processing, agriculture, and chemical detection.

BACKGROUND OF THE INVENTION

A well-appreciated need for labeling exists in society. Labeling is a fundamental basis for tracking and identifying. Encoding can be used as a form of labeling understood by persons or equipment, as in the case of bar coding. At the microscale, however, labeling/encoding itself becomes difficult.

Strategies to encode microscale materials have accordingly received increased attention for such uses as high-throughput screening in the fields of drug discovery, genetics screening, biomedical research, and biological and chemical sensing. Concurrent research strategies for measuring an increased number of analytes while minimizing the necessary sample volume have focused on either on-chip spatially differentiated arrays or encoded beads. Large arrays have been developed for biological and/or chemical sensing purposes by making use of positional encoding to register specific analyte responses. The main advantage of using an array over a conventional single analyte sensor is the ability to process and analyze a large number of analytes simultaneously. Positional arrays, however, can suffer from slow diffusion rates and limits on the concentration ranges of analytes being sensed. An alternative approach is to use individually encoded beads.

Early attempts to encode particles used fluorescent or infrared-active molecules as binary markers. More recently, cadmium selenide quantum dots have been demonstrated as viable candidates for particle encoding based on their unique fluorescent properties. Quantum dots have the advantage over organic molecules of increased stability towards photobleaching, sharper fluorescence peaks, improved solubility characteristics, and large excitation frequency ranges. With six colors (limited to the peak width of the fluorescence in the visible range) and ten intensity levels, $10^6$ particles could theoretically be encoded. In practice, this number is difficult to obtain because of spectral overlap and sample inhomogeneities. Also, despite the increased photostability of quantum dots, fluorescence quenching is still possible, casting uncertainty on using relative intensity measurements as a reliable encoding method.

Another encoding strategy has used sub-micron metallic rods. The sub-micron metallic rods are prepared by electrodeposition of metals on a porous membrane in alternating strips of controlled thickness. Different reflection characteristics of the various metals are used as a barcode for identification purposes. Reflection spectroscopy does not have the disadvantage of photobleaching inherent with fluorophores. Additionally, fluorescent analytes do not interfere with the particle signal. Deposition of rods is a relatively complex process, however, and may be difficult to apply as an encoding strategy where, for example, a large number of codes is desirable because each rod must be brought into focus in an optical reader (such as a microscope) in order to read out the codes. There remains a need for encoding strategies at the microscale.

SUMMARY OF THE INVENTION

The invention concerns a particle having a code embedded in its physical structure by refractive index changes between different regions of the particle. In preferred embodiments, a thin film possesses porosity that varies in a manner to produce a code detectable in the reflectivity spectrum.

BRIEF DESCRIPTION OF TIRE DRAWINGS

Figure 8:
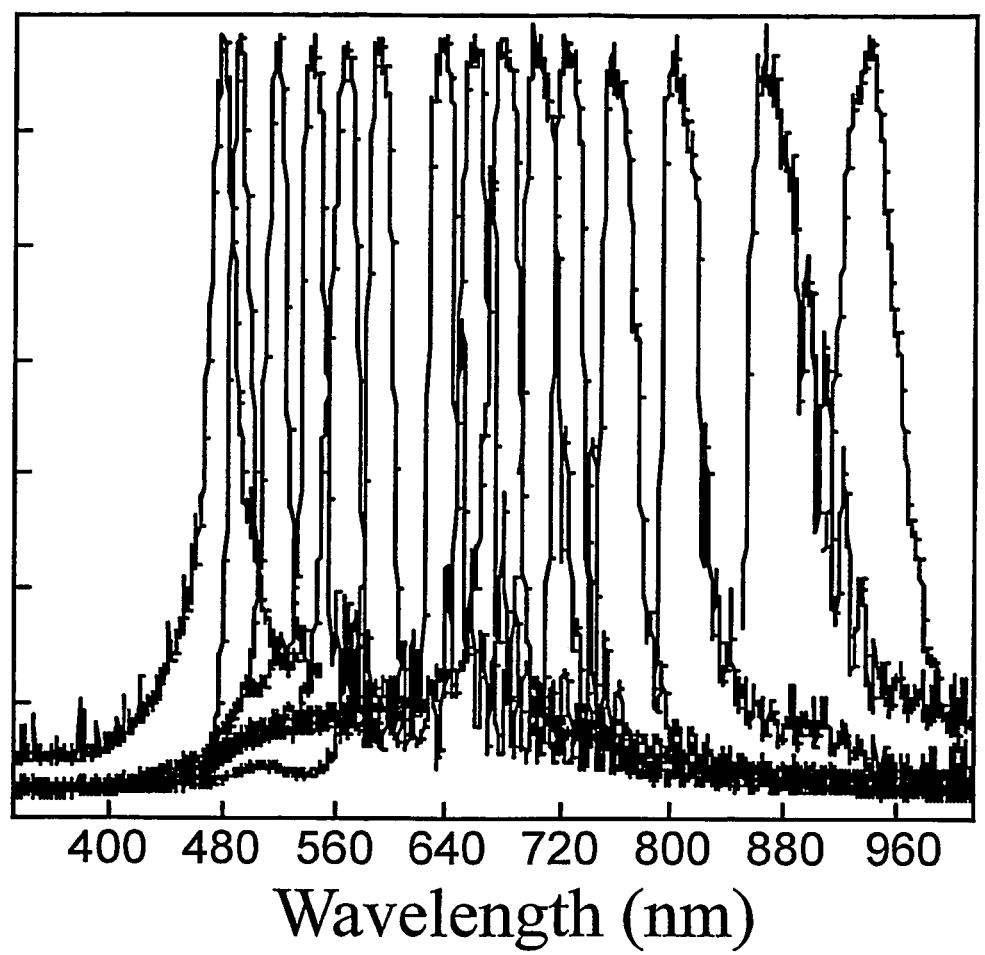
Figure 9A:
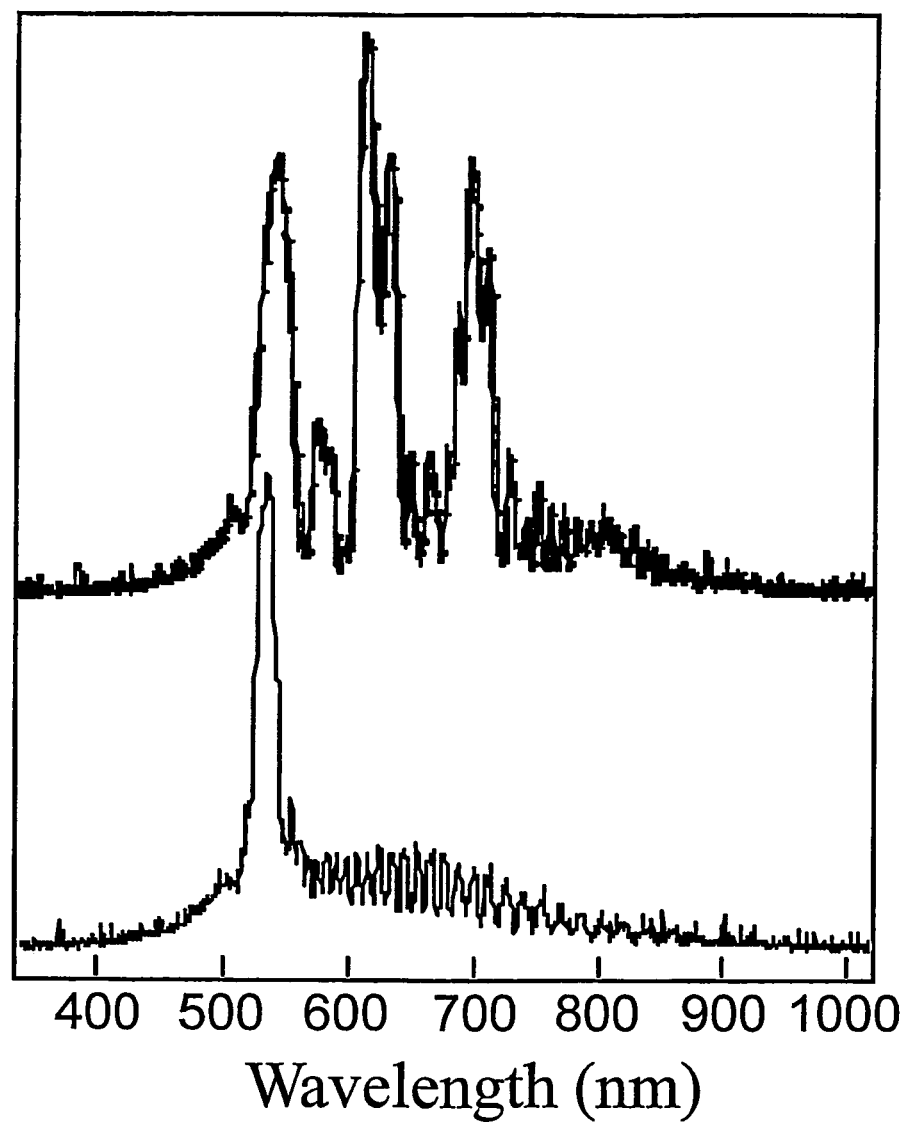
Figure 9B:
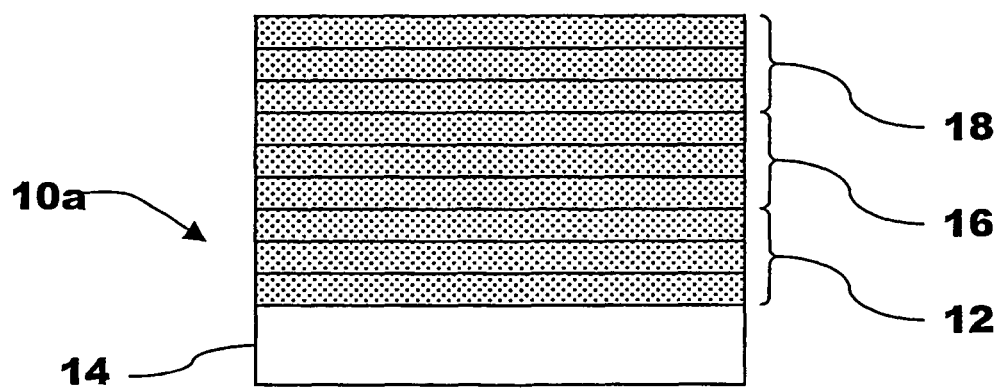
Figure 10:
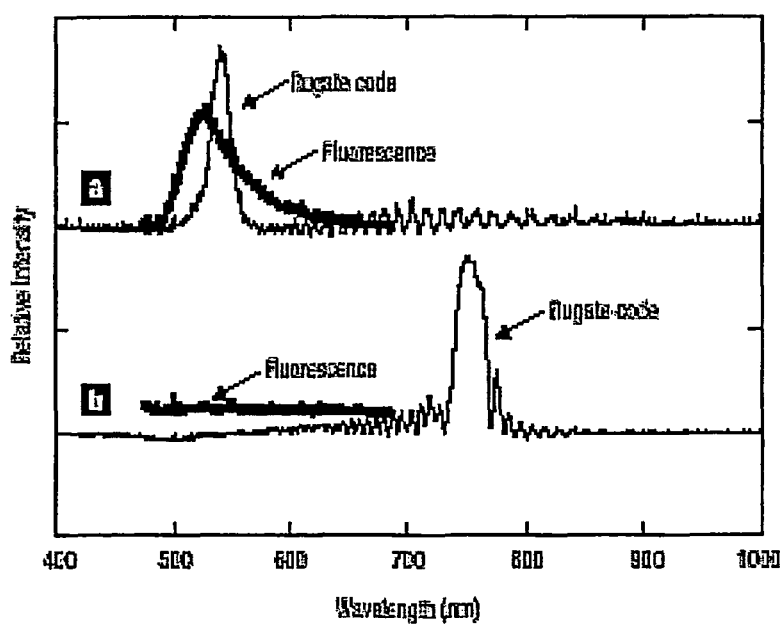

FIG. 8 plots the reflectivity spectra from 15 separately coded exemplary preferred embodiment sample particles;

FIG. 9A plots the reflectivity spectra from exemplary preferred embodiment single Rugate encoded sample particles and triply encoded Rugate sample particles;

FIG. 9B is a schematic diagram of an exemplary preferred embodiment multiple Rugate encoded particle; and FIG. 10 plots decoding results for exemplary preferred embodiment single Rugate encoded particles prepared for biological screening.

DESCRIPTION OF THE PREFERRED EMBODIMENTS

The invention concerns a particle having a code embedded in its physical structure by refractive index changes between different regions of the particle. A change in the refractive index is preferably obtained by varying porosity formed in the particle. Reflections taken from the particles produce an optical signature, in the visible and/or non-visible wavelengths. In preferred embodiments, the number of peaks, their locations, and intensities can be used to produce a high number of unique optical signatures. In preferred embodiment formation methods, a multi-layer porous encoded structure is produced by an etching process during which the etching conditions are varied during pore formation. A dicing may be conducted to form individual encoded particles having a range of small sizes, e.g., from hundreds of nanometers to hundreds of microns.

Methods and particles of the invention are applicable to a variety of industries, including but not limited to drug discovery, biological screening, chemical screening, biological labeling, chemical labeling, in vivo labeling, security identification and product marking. Various attributes of the particles and methods of the invention enable a wide range of applications in various industries. The small size of the particles facilitates ready incorporation into various hosts, e.g., products, test kits, assays, powders (such as explosives for identification) pastes, liquids; glass, paper; and any other host or system that can accept small particles. In vivo detection is enabled by biocompatible particles of the invention, which may then be queried, for example, through tissues using near infrared and infrared wavelengths that penetrate tissues.

In accordance with the aforementioned exemplary aspects and applications of the inventions, preferred embodiment particles are identified by the code inherent to the reflectivity spectrum of their varying porous structure. In another aspect of the invention, matter, e.g., biological or chemical matter, is hosted by the porous structure and the particle becomes a tag identifying the matter hosted by the pores. In another aspect of the invention, a variance in the reflectivity spectrum of an encoded particle can indicate the presence, absence or quantity of matter within the particle's pores.

Figure 1:
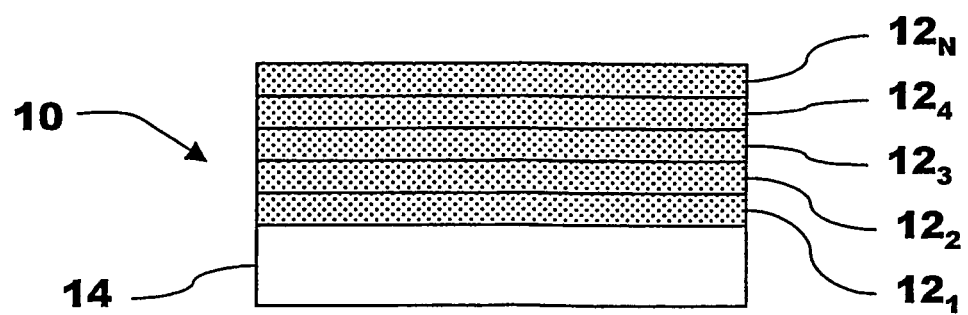
FIG. 1 is a schematic diagram of a multi-layer encoded particle of the invention.

Referring to FIG. 1, a preferred embodiment encoded particle 10 is shown in cross-section. The encoded particle 10 includes a multi-layer porous thin film having layers or regions $12_1$-$12_N$. Multi-layer, as used herein, means that there must be a plurality of regions having distinct porosity. Transitions between porosity in some embodiments may be gradual. This means that multi-layer encompasses both structures having multiple gradual transitions of porosity and structures having multiple abrupt transitions of porosity. Consistent with this definition, the layers $12_1$-$12_N$ are defined by varying porosity, which may change gradually or abruptly. Also, the use of "layer" encompasses separate deposits, for example, but also encompasses continuous structures having the varying porosity. In other words, "layer" includes but does not solely imply separate formation processes or depositions. The multi-layer porous thin film structure of layers or regions $12_1$-$12_N$ having varying porosity is shown in FIG. 1 as being formed on a substrate 14. However, embodiments of the invention include particle structures of multi-layer thin films such as the layers $12_1$-$12_N$ released from a substrate upon or from which they were initially formed. The porous layers $12_1$-$12_N$ are encoded to produce an interference pattern in the reflectivity spectrum that forms an optical signature. Light reflected at the interfaces between the porous layers $12_1$-$12_N$ interferes with light from interfaces between other ones of the layers to generate an interference pattern in the reflectivity spectrum. Particles 10 of the invention may be specifically encoded by controlling etching conditions and layer thicknesses during formation of the particle 10. The refractive index at layer interfaces, chemical composition, and thickness of each layer $12_1$-$12_N$ affects the optical signature generated by a particular particle. Thus, varying the relative porosity between layers in an individual particle (to affect the refractive index) and varying the layer thickness during formation of the particle 10 permits the tailoring of particular optical signatures in the reflectivity spectrum. Porosity also affects the intensity of peaks in the reflectivity spectrum, providing additional encoding potential.

The porous layers $12_1$-$12_N$ may be formed of any porous semiconductor or insulator. In preferred embodiment particles of the invention, porous silicon is used to form the layers $12_1$-$12_N$. Controlled anodic etching of crystal silicon in hydrofluoric acid solution permits control of both the porosity and thickness of porous layers $12_1$-$12_N$. The time of etching controls the thickness of a porous layer, while the etching current density controls the porosity. The thicknesses and porosities of layers $12_1$-$12_N$ are varied with respect to each other to produce a particular optical signature.

Variance in the porosity and thicknesses may in some embodiments be arbitrary, and in other embodiments follow a periodic pattern. In some embodiments, the porosity may vary gradually and in others the porosity may change abruptly from layer to layer. Porous silicon is a preferred material for the layers $12_1$-$12_N$. Porous silicon has a number of demonstrated advantages. For example, porous silicon has been demonstrated to be biocompatible. In addition, the surface chemistry of oxidized porous silicon is effectively that of silica. Accordingly, the surface chemistry is well understood for biochemical derivatization and ligand immobilization.

In preferred embodiments, the layers $12_1$-$12_N$ are formed to include a receptor material within the porous structure. The purpose of the receptor is to bind a particular analyte of interest. Exemplary receptors (also referred to as binders) are disclosed, for example, in U.S. Pat. No. 6,248,539 entitled "Porous Semicoductor Based Optical Interferometric Sensor". Receptor molecules may be adsorbed or otherwise associated with the porous silicon layers $12_1$-$12_N$ by any approach that leads to the tethering of the receptor molecules to the porous layers $12_1$-$12_N$. This includes, without limitation, covalently bonding the receptor molecules to the semiconductor, ionically associating the receptor molecules to the layers, adsorbing the receptor molecules onto the surface of the layers, or other similar techniques. Association can also include covalently attaching the receptor molecules to another moiety, which is in turn covalently bonded to the porous layers $12_1$-$12_N$, or binding the target molecule via hybridization or another biological association mechanism to another moiety which is coupled to the porous layers $12_1$-$12_N$. Specific additional examples include receptor ligands that have been attached to porous silicon layers to produce biosensors. An analyte bound to a particle 10 of the invention becomes identifiable and traceable by the encoding provided by the particle 10.

Figure 2A:
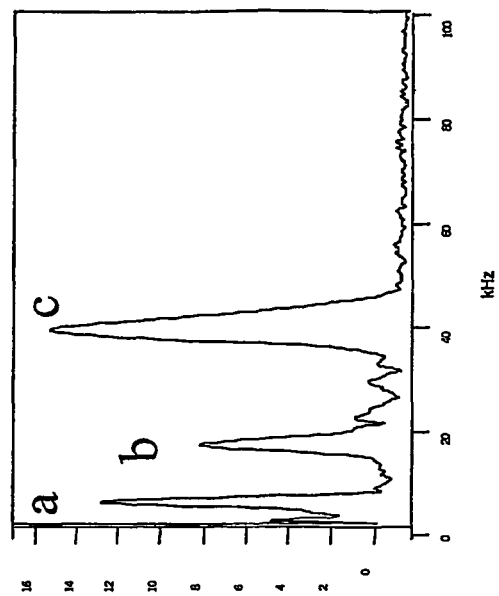
FIGS. 2A and 2B illustrate a preferred embodiment Fourier transform particle decoding.
Figure 2B:
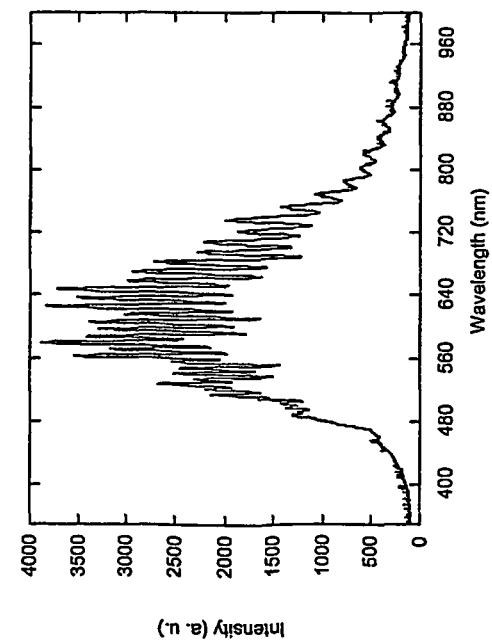

Encoding is possible for both intensity and wavelength properties of multi-layer films $12_1$-$12_N$. A preferred embodiment is a particle 10 having multi-layer films $12_1$-$12_N$ that have mismatched optical thicknesses. Optical thickness is defined as the refractive index of a layer multiplied by its metric thickness. Referring to FIGS. 2A and 2B, a particle 10 encoded in such a manner reveals an optical signature in a Fourier transform of the resulting reflectivity interference spectrum. An exemplary resulting interference spectrum is shown in FIG. 2A. The Fourier transform shown in FIG. 2B reveals an optical signature with well-resolved peaks. Particles 10 may be set to have a distinct series of peaks (a, b, c).

The intensity of peaks in the reflectance spectrum is controlled by the refractive index at interfaces between layers $12_1$-$12_N$, determined by a change in porosity between adjacent layers. Such change may be gradual or sharp. The position of peaks is controlled by adjusting layer thicknesses. Additional encoding is possible by variation of the relative intensities of each reflectivity peak, which can be engineered into particles 10 of the invention by adjustment of the electro chemical etch parameters to control porosity of the layers $12_1$-$12_N$. Accordingly, an N-layer particle 10 having A resolvable positions for each peak and B resolvable intensities can encode $(A*B)^N$ particles. Additionally, a particle 10 having N peaks with A resolvable positions for each peak with any combination of order of relative intensities can encode one of $N!(A)^N$.

Another encoding strategy involves periodic structures. Exemplary periodic structures include particles 10 having layers $12_1$-$12_N$ configured by porosity and thickness to form a Bragg stack or a Rugate filter. Bragg stacks, for example, may be generated by alternating layers having matched optical thicknesses. A Bragg stack defined by varying porosity layers $12_1$-$12_N$ in a particle 10 of the invention will produce peaks in the reflectivity spectrum with full width half maximum peaks in the reflectivity spectrum that are very well resolved, e.g., ~10 nm. Rugate filters produced by variation of the refractive index of the interfaces through multi-layer structures $12_1$-$12_N$ also generate similarly narrow peaks in the reflectivity spectrum while also suppressing side bands and higher order reflections.

Figure 3A:
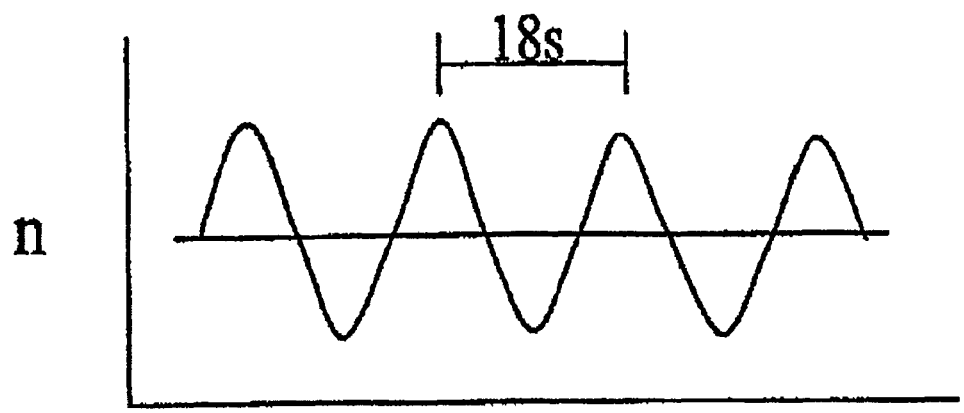
FIG. 3A illustrates an exemplary etching waveform for a preferred embodiment method of Rugate particle encoding.
Figure 3B:
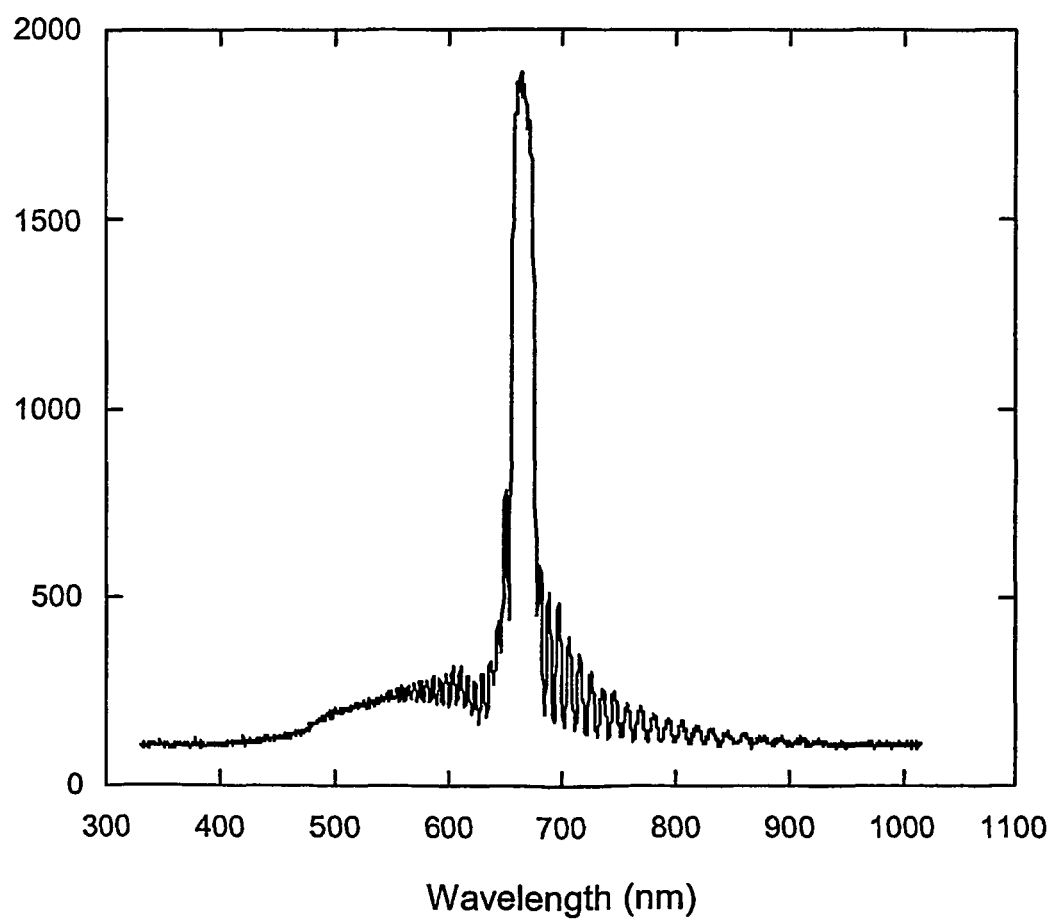
FIG. 3B illustrates a preferred embodiment Rugate particle decoding.

FIGS. 3A and 3B illustrate a preferred embodiment Rugate particle encoding strategy. A Rugate encoded particle may be created by etching a semiconductor or insulator with a periodic variance of etching conditions, such that the refractive index in the material varies in a sinusoidal (or apodised sinusoidal) function. The structures can be generated by etching the silicon wafer with a pseudo-sine current waveform. FIG. 3A indicates that a period for an exemplary sine wave variation of etching current density (n) in an etch used to produce the exemplary embodiment was 18 seconds. As seen in FIG. 3B, a well-resolved narrow peak results from the encoding. The intensity and location of the peak can be varied with layer thickness and refractive index.

Figure 4:
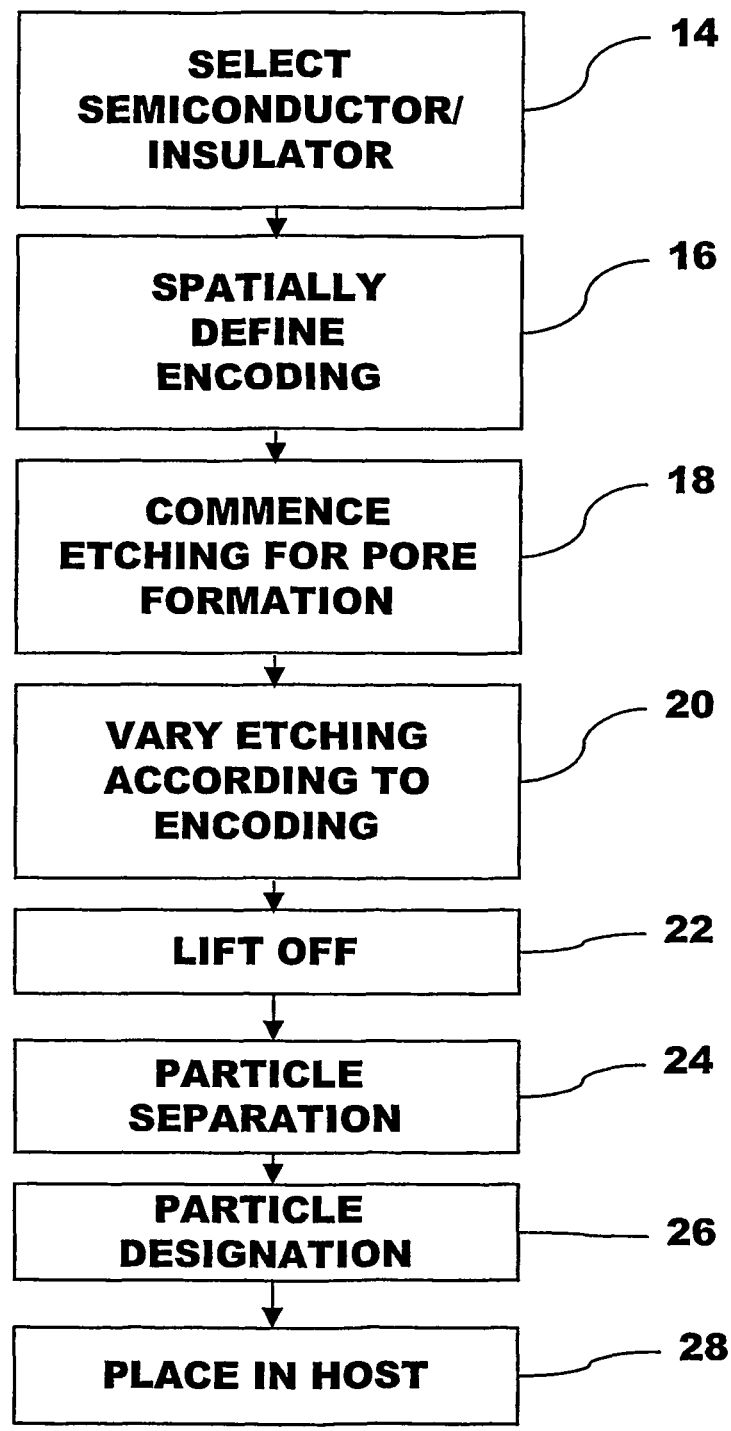
FIG. 4 illustrates a preferred embodiment method of fabricating encoded particles.

Referring now to FIG. 4, a preferred method for forming an encoded porous particle 10 is shown. A suitable semiconductor or insulator, e.g., a silicon wafer, is selected for processing (step 14). For example, silicon wafers may be cut to size and be masked to have portions exposed for etching. An exemplary suitable silicon material is a single crystalline silicon wafer. Spatial encoding is then defined (step 16). The spatial encoding defines a range of codes over the material to be etched. Conducting a spatially resolved etch allows codes to be programmed in particle-sized sections of the wafer. An exemplary spatially resolved etch is disclosed in U.S. Pat. No. 5,318,676, entitled "Photolithographic fabrication of luminescent images on porous silicon structures", published Jun. 7, 1994. In an alternative process, the step of spatial defining (step 16) is omitted. For example, a single wafer or an area of wafer could be etched to include particles having a single code. In that case, other wafers could be etched to have particles having a different code. Anodic etching is then commenced, for example, in an aqueous solution of hydrofluoric acid and ethanol (step 18). Etching is then conducted with etching conditions varying according to the defined encoding strategy (step 20). A code or codes of the invention are etched into the wafer. The traverse (vertical direction in FIG. 1) encoded but still connected particles may be lifted off from the silicon wafer (step 22), for example by a high level of electropolishing current. Areas between spatially defined etch sections may be cut to separate differently encoded wafer sections. Individual particles are then separated (step 24) in a dicing that may be conducted, for example, by mechanical agitation or ultrasonic fracturing. The particle separation (step 24) preferably produces micron-sized particles, e.g., particles in a range from a few hundred nanometers to a few hundred micrometers. A step of particle designation (step 26) may be conducted after the particle separation (step 24) or subsequent to step 20 or step 22. Particle designation may comprise, for example, chemical modification of the porous multi-layer structure $12_1$-$12_N$ for specific biological, biomedical, electronic, or environmental applications. As an example, the particles can be modified with a receptor for a desired analyte or with a targeting moiety (such as a sugar or a polypeptide). Additionally, binding can be signaled for example, by fluorescence labeling of analytes or analyte autofluoresence. In use of particle 10, the particle can be identified by its optical signature upon binding of the designated targeted analyte. This step of designation may also be omitted in embodiments of the invention.

In other embodiments of the invention, encoded particles can be placed into a suitable hosts, namely any liquid, powder, dust, or other material that will hold encoded micron sized particles of the invention. Particles placed in hosts, for example, could be used to identify the source of a manufactured powder such as an explosive. Another potential host is an animal. Particles of the invention being biocompatible may be implanted in vivo into an animal host. The reflectivity spectrum of preferred embodiment porous silicon particles 10 of the invention, for example, encompasses the visible, near infrared, and infrared spectra. This presents the opportunity to sense the code of a particle of the invention through barriers such as living tissue.

Example Embodiments and Experimental Data

Example embodiments of the invention will now be discussed. Experimental data is included for the purpose of illustrating to artisans the potential of the invention. Where given, equipment is specified only to allow artisans to understand experimental data reported herein. Commercial embodiment devices of the invention may take substantially different form, permitting low cost mass manufacturing, for example.

A first example embodiment is stand-off detection. This is a chemical detection technique to identify an analyte from a distance. A particle 10 of the invention includes a receptor to sense a particular analyte. Both the code of the particle and an indication of binding of the analyte can be detected in the reflectivity spectrum, for example, with use of a low power laser. The receptor, for example, can be specific to sense biomolecules or to attach the encoded particle to a cell, spore, or pollen particle.

A test of stand-off detection was conducted with exemplary encoded multi-layer porous silicon films. The multi-layered porous silicon films were prepared by an electrochemical etch of a (100) oriented polished Si wafer ($p^{++}$-type, B doped; <1 in mΩ-cm resistivity) in a 1:3 ethanol:48% aqueous HF solution. The etching current density was modulated periodically with a pseudo-sine wave (between 11.5 and 34.6 mA/cm$^2$) to generate a sinusoidally varying porosity gradient. The films were removed from the substrate by applying a 30 second electropolishing pulse of current density of 600 mA/cm$^2$. The freestanding films were then made into particles by mechanical grinding or by ultrasonic fracture to produce particles of sizes ranging from several hundred nanometers to a few hundred microns. The optical reflectivity spectrum in FIG. 5 approximates a Rugate filter, displaying a sharp reflection maximum at a wavelength and source-sample-detector angle that satisfies the Bragg equation and appropriate phase matching condition.

Figure 5:
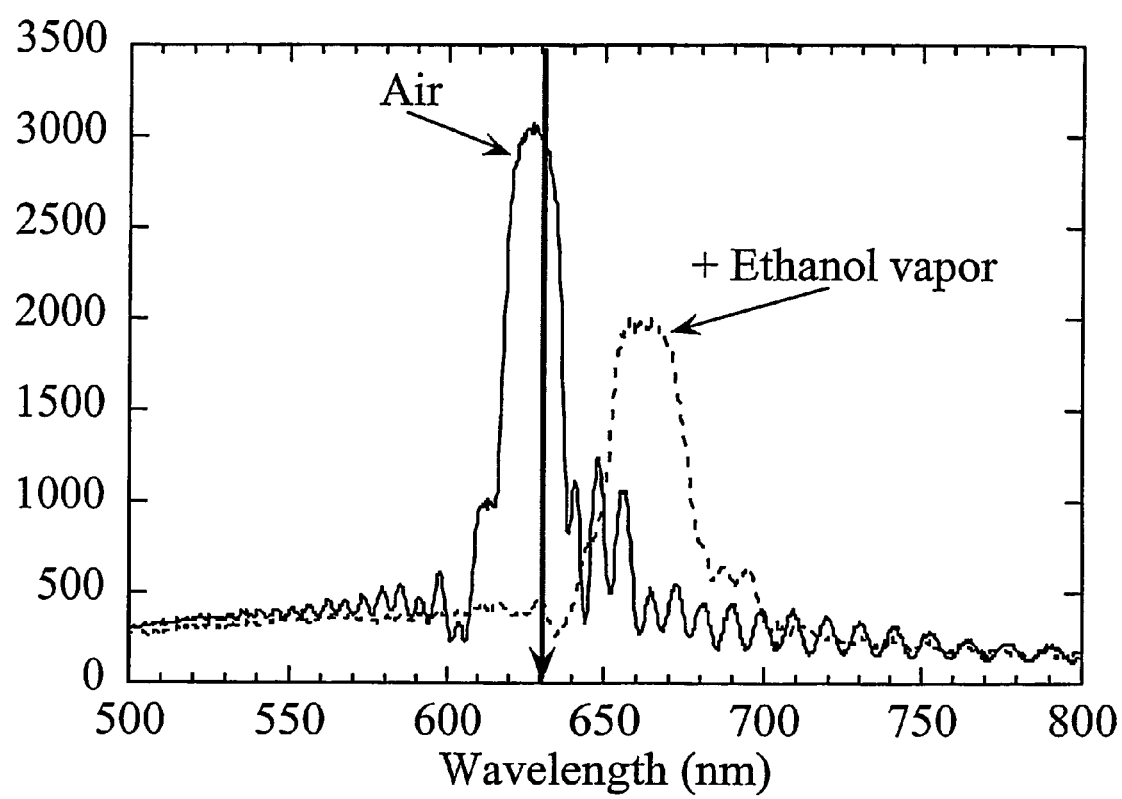
FIG. 5 shows the optical reflectivity spectrum of a single preferred embodiment encoded particle in laboratory air (solid line) and in air containing a small amount of ethanol vapor (dashed line)

The particles were immobilized on a glass plate and mounted in a gas dosing chamber fitted with an optical window and Baratron pressure gauge. The particles were illuminated with a 10 MW He/Ne laser. The as-formed particles strongly reflect the 632 nm light of the He/Ne laser at a wavelength in air, as seen in FIG. 5. The spectral position of the laser used to acquire the data presented in FIG. 5 is shown for comparison (vertical arrow). The data were taken using an Ocean Optics CCD visible spectrometer at the focal plane of an optical microscope. When exposed to analyte vapors, capillary condensation causes the reflectivity spectrum of the particles to shift to longer wavelengths due to an increase in the refractive index of the porous medium and the particles are observed to go dark.

Figure 6:
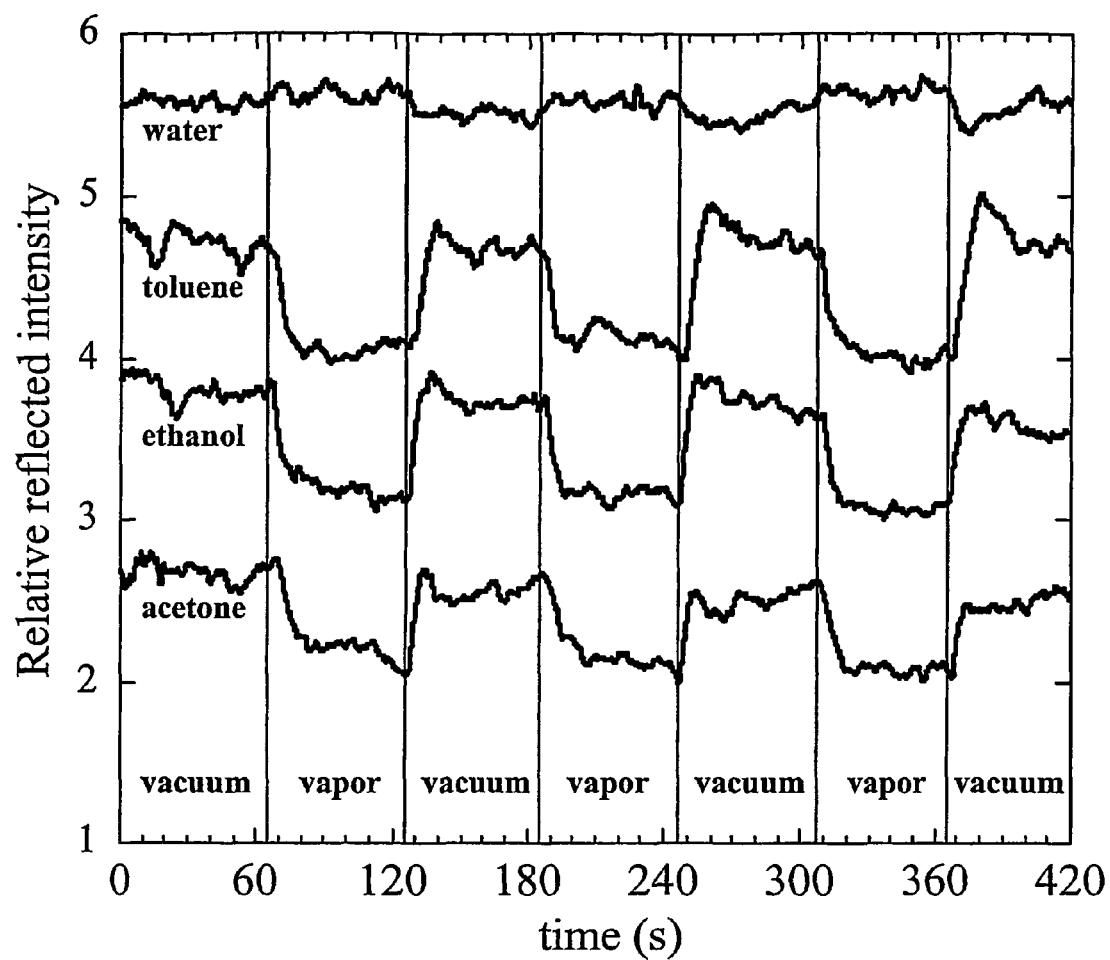
FIG. 6 shows the intensity of reflected laser light (632 nm) from a preferred embodiment encoded porous silicon Rugate particle measured for three exposure/evacuation cycles using (from bottom to top as indicated) acetone, ethanol, toluene and water analytes at their saturation vapor pressures.

The relative change in light intensity simultaneously reflected from many of the particles was quantified at a fixed wavelength (632 nm) for a series of condensable analyte vapors, as seen in FIG. 6. The vapor pressure at 25° C. for each of these analytes is 222, 60, 28, and 24 Torr, respectively. Relative reflected light intensity was measured as the photocurrent from an amplified Si photodiode mounted at the objective of the 8-inch Schmidt-Cassegrain collection optics. The sample was 20 m from the laser and detection optics. Spectra are offset along the y-axis for clarity. The vapors were all introduced to the exposure chamber at their saturation vapor pressures. The intensity of reflected light was measured at a distance of 20 m in the presence of normal fluorescent room lighting using chopped light and phase-sensitive detection (Stanford Instruments SR-510 lock-in amplifier). No other optical or electronic filtering was used. The specificity of adsorption and/or microcapillary condensation at porous Si surfaces depends dramatically on the surface chemistry, and the hydrogen-terminated, hydrophobic as-formed material used in the experiments has a much greater affinity for hydrophobic versus hydrophilic analytes. Thus, the particles are relatively insensitive to water vapor at a partial pressure comparable to that used for the more hydrophobic organic analytes. No attempt was made to provide acoustic or vibrational isolation of the sample or optics, and most of the noise observed in the data is attributed to laboratory vibrations. Sensitivity should be further enhanced using a near infrared laser light source, where background radiation and atmospheric adsorption and scattering are less significant.

Another preferred exemplary application of the invention is for biomolecular screening via the encoded particle 10 of the invention. Millions of codes are possible with a small number of layers. A simple antibody-based bioassay using fluorescently tagged proteins has been tested. Periodic Rugate style encoding was used as described above with respect to the exemplary chemical sensing embodiments. By masking the wafer before etching, well-defined slabs of particles were generated, as seen in FIG. 7.

Figure 7:
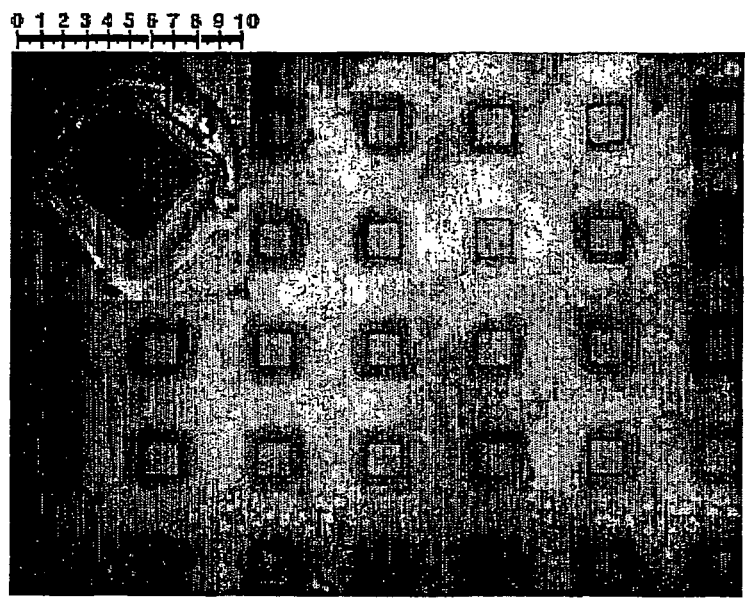
FIG. 7 is an image of exemplary preferred embodiment encoded particles formed in a wafer by a spatially defined, periodically varying etch.

The FIG. 7 particles were prepared to display a photonic spectral maximum at 632 nm. The scale in the inset (reproduced above the figure for clarity) corresponds to 2 µm per small division. The multi-layered encoded particles generated in this fashion display a very sharp line in the optical reflectivity spectrum. This line can appear anywhere in the visible to near-infrared spectral range, depending on the waveform used in the programmed etch.

Exemplary waveforms for 15 separate codes are shown in FIG. 8. FIG. 8 shows the reflectivity spectra of 15 poroussilicon multi-layered samples prepared using a sinusoidal etch (Rugate encoded structure). Each of the samples contains a single Rugate frequency code. Spectra were obtained using a Cambridge Instruments microscope with a 70× objective. The sample was illuminated using a tungsten lamp, and the reflected light spectrum was measured with an Ocean Optics SD2000 CCD (charge-coupled device) spectrometer. The sample particles were prepared by anodically etching $p^{++}$ type, B-doped, (100)-oriented silicon (resistivity<1 $m\Omega$–$cm^2$) in a solution of 48% aqueous HF:ethanol (3:1 by volume). Typical etch parameters for a Rugate structure used in a pseudosinusoidal current waveform oscillating between 11.5 and 19.2 mA $cm^{-2}$ with 50 repeats and a periodicity of 18 s. Films were removed from the substrate using a current pulse of 460 mA $cm^{-2}$ for 40 s. Lithographically defined particles were prepared by applying an S-1813 photoresist (Shipley) to the wafer before the electrochemical etch (spin coated at 4,000 r.p.m. for 60 s, soft-baked at 90° C. for 2 min., ultraviolet-exposed using a contact mask aligner, hard-baked at 120° C. for 30 min. before development). The spectral features exemplified by FIG. 8 can be much narrower than the fluorescence spectrum obtained from a molecule or core-shell quantum dot.

FIG. 9A shows the reflectivity spectra of porous silicon Rugate encoded particles etched with a single periodicity (bottom) and with three separate periodicities (top). FIG. 9B schematically illustrates a preferred embodiment multiple encoded particle 10a, wherein there are three sets of encoded layers 12, 16, and 18. Multiple Rugate codes may be separated spatially, but also may be etched in the same physical location, as sets of multi-layers formed at different depths, each forming a separate Rugate encoding. Each of the layer sets 12, 16, and 18 includes a periodically varying porosity to produce a separate Rugate, or alternatively, Bragg, code.

The example particles display peaks in the reflectivity spectrum characteristic of their multi-layered structures. The sample represented in the bottom spectrum was etched using a sinusoidal current variation between 11.5 and 19.2 mA $cm^{-2}$ with 50 repeats and a periodicity of 18 s. The triply encoded particle (triple Rugate) represented by the top spectrum was prepared using a sinusoidal current variation oscillating between 11.5 and 34.6 mA $cm^{-2}$ with a periodicity of 10 s for 20 periods (520 nm), 12 s for 45 periods (610 mm), and 14 s for 90 periods (700 nm). The approximate thickness of this sample is 15 µm. Spectra are offset along the y axis for clarity.

To test the reliability of the encoding approach in a biological screening application, we prepared two different batches of encoded particles as single Rugate structures. Both batches of particles were ozone-oxidized to improve their stability in aqueous media and to provide a hydrophilic surface. The particles were oxidized in a stream of $O_3$ diluted with compressed air. Control particles coded with a 750-nm spectral feature were treated with concentrated BSA (Sigma, 5 g in 100 ml of double-distilled water) and incubated at 37° C. under 5% $CO_2$ in air for three hours. The 540-nm-encoded test particles were exposed to 50 µg $ml^{-1}$ rat albumin in coating buffer (2.93 g $NaHCO_3$, 1.61 g $Na_2CO_3$ in 1,000 ml double-distilled water), and incubated at 37° C. under 5% $CO_2$ for two hours. The test particles were then exposed to a 1:100 dilution of primary rabbit anti-rat-albumin antibody in a concentrated solution of BSA at 37° C. under 5% $CO_2$, for one hour. Both batches of particles were then mixed together and incubated for one hour in the presence of FITC-(fluorescein isothiocyanate) conjugated goat anti-rabbit immunoglobulin-G in a BSA solution. Detection of analyte binding to the encoded particles was then performed by fluorescence and spectral reflectance microscopy.

Decoding results are shown in FIG. 10. Decoding, performed on 16 particles, yielded the following results: among eight green fluorescent particles, eight particles were positively decoded as belonging to the functionalized rat albumin batch (plot A in FIG. 10). Among the eight non-luminescent particles, six particles were correctly decoded (plot B in FIG. 10), one particle displayed the incorrect code and one particle was unreadable. Presumably, the particle that displayed the incorrect code belonged to the first batch but was not sufficiently functionalized with rat albumin to generate fluorescence in the antibody assay. This is understandable because in the experiment the rat albumin was not covalently attached to the silica-coated particles. A variety of stable chemical modification chemistries have been developed for oxidized and non-oxidized porous silicon, and some of these have been demonstrated with specific antibodies or receptors. Thus, the issue of immobilizing biochemical or chemical components is easily addressable. Additionally, chemical modification can prevent corrosion in aqueous media, which may otherwise lead to undesirable shifts in the optical code and/or unreadable particles. In the conducted experiments, no passivating chemical treatments, other than ozone oxidation to generate a layer of silica, were performed, and upon immersion in basic aqueous media the spectral codes were observed to shift between 0 and 50 nm depending on the incubation times.

The layered porous-silicon encoded structures offer several advantages over existing encoding methodologies. Porous-silicon encoded structures can be constructed that display features spanning the visible, near-infrared and infrared regions of the spectrum. In addition, the reflectivity spectra of Rugate filters can exhibit much sharper spectral features than can be obtained from a gaussian ensemble of quantum dots. Thus, more codes can be placed in a narrower spectral window with the porous encoded structures. Unlike encoding schemes based on stratified metallic nanorods, fluorescence or vibrational signatures, encoded particles of the invention can be probed using light diffraction techniques; thus it is not necessary to use imaging optics in order to read the codes. Encoded particles may be assayed using a conventional fluorescence tagging technique, and sensitive chemical and biochemical detection can also be built into the optical structure of the encoded particles, eliminating the need for fluorescent probes and focusing optics. In addition, because preferred embodiment oxidized porous-silicon encoded particles present a silica-like surface to the environment, they do not readily quench luminescence from organic chromophores, and they can be handled and modified using the chemistries developed for glass bead bioassays. Silicon-based encoded particles may be readily integrated with existing chip technologies.

The use of encoded silicon particles of the invention in medical diagnostic applications has advantages over organic dyes or quantum dots. In vivo studies have shown the biocompatibility of porous silicon, as well as the long-term stability of reflectance data from multilayer structures. Additionally, the possibility of optically addressing particles at near-infrared, tissue-penetrating wavelengths without the losses associated with low fluorescence quantum yields makes these materials amenable to in vivo diagnostics. Finally, because the porous codes are an integral and orderly part of the porous structure, it is not possible for part of the code to be lost, scrambled or photobleached, as can occur with quantum dots or fluorescent molecules.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A freestanding optically encoded particle, comprising:
a first porous layer having a predetermined first porosity and thickness; and
a plurality of n additional porous layers having predetermined thicknesses and porosities, at least one of which has a predetermined porosity differing from said first porosity; wherein
said predetermined porosities and thicknesses of said first porous layer and said n additional porous layers are configured to produce an interference pattern in the reflectivity spectrum having a distinct series of peaks such that the interference pattern forms an optical signature having a particular predetermined code determined by the porosities and thicknesses of said first porous layer and said n additional porous layers a receptor or targeting moiety for binding a predetermined analyte, wherein said receptor or targeting moiety is within one or more of said first porous layer and said n additional porous layers; and wherein
the particle has a diameter of a few hundred microns or less and is freestanding separated from any substrate.

2. The particle of claim 1, wherein the particle has a diameter in the range from a few hundred nanometers to a few hundred microns.

3. The particle of claim 1, wherein said first porous layer and said n additional porous layers have a matched optical thickness, wherein optical thickness comprises the product of refractive index and layer thickness.

4. The particle of claim 1, wherein said interference pattern in the reflectivity spectrum extends beyond the visible spectrum.

5. The particle of claim 1, wherein said first porous layer and said n additional porous layers alternate periodically and form a Bragg stack.

6. The particle of claim 1, wherein said first porous layer and said n additional porous layers form a Rugate reflector.

7. The particle of claim 1, wherein said first porous layer and said n additional porous layers are formed from a semiconductor.

8. The particle of claim 7, wherein said semiconductor comprises silicon.

9. The particle of claim 1, wherein said first porous layer and said n additional porous layers are formed from an insulator.

10. A method for identification of an analyte bound to an encoded particle of claim 1, the method comprising steps of:
associating the encoded particle with the analyte;
generating an interference pattern in the reflectivity spectrum by illumination of the particle;
determining said particular predetermined code from the interference pattern;
identifying the analyte based upon said step of determining.

11. The method according to claim 10, wherein the targeting moiety is a sugar or polypeptide.

12. The method according to claim 10, further comprising a step of signaling binding of an analyte by fluorescence labeling or analyte autofluorescence.

13. A method for identification of an analyte bound to a particle of claim 1, the method comprising steps of:
associating the encoded particle with the analyte;
generating an interference pattern in the reflectivity spectrum by illumination of the particle;
determining said particular predetermined code from the interference pattern; and identifying the analyte based upon said step of determining, wherein the receptor or targeting moiety is a sugar or polypeptide.

14. A method for identification of an analyte bound to a particle of claim 1, the method comprising steps of:
associating the encoded particle with the analyte;
generating an interference pattern in the reflectivity spectrum by illumination of the particle;
determining said particular predetermined code from the interference pattern; and
identifying the analyte based upon said step of determining, wherein the receptor or targeting moiety is a sugar or polypeptide.

15. A method for identification of an analyte bound to a particle of claim 1, the method comprising steps of:
associating the encoded particle with the analyte;
binding of an analyte by fluorescence labeling or analyte autofluorescence;
generating an interference pattern in the reflectivity spectrum by illumination of the particle;
determining said particular predetermined code from the interference pattern; and
identifying the analyte based upon said step of determining, wherein the receptor or targeting moiety is a sugar or polypeptide.

16. A freestanding encoded micron-sized porous particle having a particular predetermined code embedded in its physical porous structure by refractive index changes between different porous regions of the particle and a receptor or targeting moiety within said porous structure, wherein the physical porous structure has a plurality of layers some of which have separate predetermined mismatched optical thicknesses and the particle has a diameter of a few hundred microns or less and is freestanding separated from any substrate.

17. The encoded micron-sized particle of claim 16, wherein different regions of the particle have different thickness.

18. The particle of claim 16, wherein said receptor is a receptor for a biological analyte.

19. The particle of claim 16, wherein said receptor is a receptor for a chemical analyte.

20. The particle of claim 16, wherein said receptor is a receptor for a gaseous analyte.

21. The particle of claim 16, further comprising a fluorescence tag for assaying the particle.

22. The particle of claim 16, wherein said porous structure consists of porous silicon.

23. A method for identification of an analyte bound to a particle of claim 16, the method comprising steps of:
associating the encoded particle with the analyte;
generating an interference pattern in the reflectivity spectrum by illumination of the particle;
determining said particular predetermined code from the interference pattern; and
identifying the analyte based upon said step of determining.

24. A method for identification of an analyte bound to or a host including a particle of claim 16, the method comprising steps of:
associating the encoded particle with the analyte;
generating an interference pattern in the reflectivity spectrum by illumination of the particle;
determining said particular predetermined code from the interference pattern; and
identifying the analyte based upon said step of determining, wherein the receptor or targeting moiety is a sugar or polypeptide.

25. A method for identification of an analyte bound to a particle of claim 16, the method comprising steps of:
associating the encoded particle with the analyte;
binding of an analyte by fluorescence labeling or analyte autofluorescence;
generating an interference pattern in the reflectivity spectrum by illumination of the particle;
determining said particular predetermined code from the interference pattern; and
identifying the analyte based upon said step of determining, wherein the receptor or targeting moiety is a sugar or polypeptide.

26. An optically encoded particle consisting of:
a first porous layer having a predetermined first porosity; and
a plurality of n additional consecutive porous layers upon said first porous layer, said n additional consecutive porous layers having predetermined thicknesses and porosities and at least one of said n additional consecutive porous layers having a porosity differing from said first porosity and a receptor or targeting moiety within one or more of said first porous layer and said n additional consecutive porous layers; wherein
said first porous layer and said n additional porous layers are configured to produce an interference pattern in the reflectivity spectrum having a distinct series of peaks such that the interference pattern forms an optical signature having a particular predetermined code determined by the porosities and thicknesses of said first porous layer and said n additional porous layers, and wherein
the particle has a diameter of a few hundred microns or less and is freestanding separated from any substrate.

27. The particle of claim 1, wherein said predetermined thickness of said first porous layer and said predetermined thicknesses of said n additional porous comprise a plurality of thicknesses that are varied with respect to each other.

* * * * *

UNITED STATES PATENT AND TRADEMARK OFFICE
CERTIFICATE OF CORRECTION

PATENT NO. : 8,765,484 B2  
APPLICATION NO. : 10/503217  
DATED : July 1, 2014  
INVENTOR(S) : Michael J. Sailor Page 1 of 1

It is certified that error appears in the above-identified patent and that said Letters Patent is hereby corrected as shown below:

In the Specification:

Col. 2, line 20    Please delete "TIRE" and insert --THE-- therefor.

Col. 6, line 66    Please delete "MW" and insert --mW-- therefor.

In the Claims:

Claim 27, Col. 12, line 51    After "additional porous" please insert --layers--.

Signed and Sealed this  
Seventh Day of April, 2015

Michelle K. Lee  
*Director of the United States Patent and Trademark Office*